United States Patent [19]
Morales

[11] Patent Number: 6,009,614
[45] Date of Patent: Jan. 4, 2000

[54] STENT CRIMPING TOOL AND METHOD OF USE

[75] Inventor: Stephen A. Morales, Mountain View, Calif.

[73] Assignee: Advanced Cardiovascular Systems, Inc., Santa Clara, Calif.

[21] Appl. No.: 09/063,905

[22] Filed: Apr. 21, 1998

[51] Int. Cl.[7] .......................... A61M 29/00; B23P 11/00; B23P 19/02
[52] U.S. Cl. ................................ 29/516; 29/270; 29/282; 29/407.08; 29/235; 606/1; 606/108; 606/198; 623/1
[58] Field of Search ................................ 29/516, 407.08, 29/282, 280, 715, 423, 517, 234, 235, 283, 269, 270, 237; 606/1, 108, 198; 623/1; 72/402

[56] References Cited

U.S. PATENT DOCUMENTS

| | | |
|---|---|---|
| 696,289 | 3/1902 | Williams . |
| 3,568,495 | 3/1971 | Duffield et al. . |
| 4,043,172 | 8/1977 | Schmitton . |
| 4,379,397 | 4/1983 | Langr . |
| 4,468,224 | 8/1984 | Enzmann et al. . |

(List continued on next page.)

FOREIGN PATENT DOCUMENTS

| | | |
|---|---|---|
| 159065 | 2/1921 | United Kingdom . |
| WO 98/14120 | 4/1998 | WIPO . |
| WO 98/19633 | 5/1998 | WIPO . |

OTHER PUBLICATIONS

U.S. application No. 08/795,335 filed Feb. 4, 1997.
U.S. application No. 08/837,771 filed Apr. 22, 1997.
U.S. application No. 08/089,936 filed Jul. 15, 1997.
U.S. application No. 08/962,632 filed Nov. 3, 1997.

*The eXTraordinary Stent*, C.R. Bard Brochure (Undated).

*Primary Examiner*—S. Thomas Hughes
*Assistant Examiner*—John Preta
*Attorney, Agent, or Firm*—Fulwider Patton Lee & Utecht, LLP

[57] ABSTRACT

A tool and method for enabling substantially uniform and tight crimping of an intravascular stent onto a balloon catheter assembly. The crimping tool is constructed from a rigid cylindrical chassis sealed at both ends, having a hollow interior containing an elastic tube that partially occupies the interior. A piston abuts the elastic tube and forms a hermetically sealed chamber behind the piston and a closed end of the chassis. A port connected to an indeflator and positioned on the chassis provides an inlet into and out of the chamber. A stent that is loaded onto the balloon portion of the catheter is inserted through a central opening in another end of the chassis to position the stent catheter assembly within the axial space inside the elastic tube. The indeflator injects a fluid into the chamber thereby increasing its pressure which in turn displaces the piston into the elastic tube compressing the tube longitudinally. The elastic tube decreases in length and expands in thickness radially to crimp the stent onto the balloon catheter. Once pressure is relieved from the chamber, the piston moves away from the elastic tube, which restores to its original shape. The crimped stent and catheter can then be withdrawn. The piston may be driven by a power screw in place of fluid pressure.

28 Claims, 3 Drawing Sheets

U.S. PATENT DOCUMENTS

| | | |
|---|---|---|
| 4,576,142 | 3/1986 | Schiff . |
| 4,644,936 | 2/1987 | Schiff . |
| 4,681,092 | 7/1987 | Cho et al. . |
| 4,697,573 | 10/1987 | Schiff . |
| 4,901,707 | 2/1990 | Schiff . |
| 4,907,336 | 3/1990 | Gianturco . |
| 5,132,066 | 7/1992 | Charlesworth et al. . |
| 5,133,732 | 7/1992 | Wiktor . |
| 5,183,085 | 2/1993 | Timmermans . |
| 5,189,786 | 3/1993 | Ishikawa et al. . |
| 5,437,083 | 8/1995 | Williams et al. . |
| 5,546,646 | 8/1996 | Williams et al. . |
| 5,626,604 | 5/1997 | Cottone, Jr. . |
| 5,630,830 | 5/1997 | Verbeek . |
| 5,653,691 | 8/1997 | Rupp et al. . |
| 5,695,515 | 12/1997 | Orejola . |
| 5,738,674 | 4/1998 | Williams et al. . |
| 5,746,764 | 5/1998 | Green et al. . |
| 5,783,227 | 7/1998 | Dunham . |
| 5,785,715 | 7/1998 | Schatz . |
| 5,795,289 | 8/1998 | Wyttenbach . |
| 5,810,838 | 9/1998 | Solar . |
| 5,836,952 | 11/1998 | Davis et al. . |
| 5,860,966 | 1/1999 | Tower . |
| 5,893,852 | 4/1999 | Morales . |

STENT CRIMPING TOOL AND METHOD OF USE

BACKGROUND OF THE INVENTION

The present invention relates to an apparatus for loading a tubular graft, such as a stent, onto the distal end of a catheter assembly of the kind used, for example, in percutaneous transluminal coronary angioplasty (PTCA) or percutaneous transluminal angioplasty (PTA) procedures.

In typical PTCA procedures, a guiding catheter is percutaneously introduced into the cardiovascular system of a patient through the brachial or femoral arteries and advanced through the vasculature until the distal end of the guiding catheter is in the ostium. A guide wire and a dilatation catheter having a balloon on the distal end are introduced through the guiding catheter with the guide wire sliding within the dilatation catheter. The guide wire is first advanced out ofthe guiding catheter into the patient's coronary vasculature and the dilatation catheter is advanced over the previously advanced guide wire until the dilatation balloon is properly positioned across the arterial lesion. Once in position across the lesion, a flexible and expandable balloon is inflated to a predetermined size with a radiopaque liquid at relatively high pressures to radially compress the atherosclerotic plaque of the lesion against the inside of the artery wall and thereby dilate the lumen of the artery. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

In angioplasty procedures of the kind referenced above, restenosis of the artery may develop over time, which may require another angioplasty procedure, a surgical bypass operation, or some other method of repairing or strengthening the area. To reduce the likelihood of the development of restenosis and to strengthen the area, a physician can implant an intravascular prosthesis for maintaining vascular patency, commonly known as a stent, inside the artery at the lesion. The stent is crimped tightly onto the balloon portion of the catheter and transported in its delivery diameter through the patient's vasculature. At the deployment site, the stent is expanded to a larger diameter, often by inflating the balloon portion of the catheter. The stent also may be of the self-expanding type.

Since the catheter and stent travel through the patient's vasculature, and probably through the coronary arteries, the stent must have a small delivery diameter and must be firmly attached to the catheter until the physician is ready to implant it. Thus, the stent must be loaded onto the catheter so that it does not interfere with delivery, and it must not come off the catheter until it is implanted.

In procedures where the stent is placed over the balloon portion of the catheter, it is necessary to crimp the stent onto the balloon portion to reduce its diameter and to prevent it from sliding off the catheter when the catheter is advanced through the patient's vasculature. Non-uniform crimping can result in sharp edges being formed along the now uneven surface of the crimped stent. Furthermore, nonuniform stent crimping may not achieve the desired minimal profile for the stent and catheter assembly. Where the stent is not reliably crimped onto the catheter, the stent may slide off the catheter and into the patient's vasculature prematurely as a loose foreign body, possibly causing blood clots in the vasculature, including thrombosis. Therefore, it is important to ensure the proper crimping of a stent onto a catheter in a uniform and reliable manner.

This crimping is often done by hand, which can be unsatisfactory due to the uneven application of force resulting in non-uniform crimps. In addition, it is difficult to visually judge when a uniform and reliable crimp has been applied.

Some self-expanding stents are difficult to load by hand onto a delivery device such as a catheter. Furthermore, the more the stent is handled the higher the likelihood of human error resulting in potentially short and long term damage to the stent, which would be antithetical to a properly crimped stent. Accordingly, there is a need in the art for a device for reliably crimping a stent onto a catheter.

There have been attempts at devising a tool for crimping a stent onto a balloon delivery catheter. An example of such a tool comprises a series of plates having substantially flat and parallel surfaces that move in a rectilinear fashion with respect to each other. A stent carrying catheter is disposed between these surfaces, which surfaces crimp the stent onto the outside of the catheter by their relative motion and applied pressure. The plates have multiple degrees of freedom and may have force-indicating transducers to measure and indicate the force applied to the catheter during crimping of the stent.

Another stent loading tool design is comprised of a tubular member housing a bladder. The tubular member and bladder are constructed to hold a stent that is to be crimped onto a balloon catheter assembly. Upon placement of the stent over the balloon portion of the catheter, a valve in the loading tool is activated to inflate the bladder. The bladder compresses the stent radially inward to a reduced diameter onto the balloon portion of the catheter to achieve a snug fit. In this way, the stent is crimped onto the distal end of a balloon catheter with a minimum of human handling. The foregoing stent crimping tools are disclosed in, for example, U.S. Pat. Nos. 5,437,083 and 5,546,646 to Williams et al.

Yet another stent crimping tool is known in the art as the BARD XT, which is actually a stent loader. It is constructed of a tubular body with a ball at one end connected to a plurality of long, thin strips passing through the rigid tubular body. An uncrimped stent is placed over the plurality of long, thin strips, which hold the stent in an expanded state. The balloon portion of a catheter is inserted into the cylindrical space formed by the plurality of strips. When the user pulls on the ball while holding the tubular body against the stent, the strips are slid from beneath the stent and the stent is transferred onto the balloon portion.

Still another conventional stent crimping tool is manufactured by JOHNSON & JOHNSON and appears similar to a hinged nutcracker. Specifically, the tool is comprised of two hand operated levers hinged at one end and gripped in the palm of the hand at the opposite end. A cylindrical opening holding a crimping tube is provided through the mid-portion of the tool to receive therein a stent loaded onto a balloon catheter. The crimping operation is performed by the user squeezing the handle thereby pressing the crimping tube which in turn pinches the stent onto the balloon catheter.

SUMMARY OF THE INVENTION

The present invention is directed to a tool operated by a pressurized fluid source such as an indeflator for crimping an intravascular stent onto a balloon catheter. In a preferred embodiment, the present invention tool comprises a rigid cylindrical shaped chassis having a hollow interior with a closed back end leading to an open front end, an end cap enclosing the open front end, the end cap including a central opening. Inside the chassis is a cylindrical shaped elastic tube disposed adjacent to the front end and having a length less than a length of the hollow interior to define a chamber adjacent to the back end of the chassis. The invention further comprises a piston that is slidably disposed within the chamber, and a port in communication with the chamber disposed between the back end of the chassis and the piston, wherein a flow through the port from the pressurized fluid source forces the piston into and axially compresses the elastic tube. In this manner, the stent is crimped onto the balloon catheter.

More precisely, after the stent is loaded onto the catheter and inserted through the central opening into the axial space within the elastic tube, the tube is compressed axially. Under compression the elastic tube encounters surface tension and outside containment by the chassis which force the tube to maintain a constant volume. Moreover, the tube by its elastic nature will attempt to maintain constant volume. To maintain that constant volume while decreasing its length, the tube displaces material radially inward into the open axial space containing the stent-catheter assembly. This changes the form of the elastic tube cross-section to a shorter and squatter configuration. The elastic tube thus converts the axial displacement of material into a radial displacement of material. Accordingly, the diameter of the axial space decreases steadily eventually compressing the stent onto the balloon catheter by a factor of $\Delta l/l_0(A_0)$, where $l_0$ is the initial length, $A_0$ is the initial cross-sectional area.

The present invention tool is operated under fluid pressure. In a preferred embodiment, the fluid pressure is generated by an indeflator wherein a fluid or gas is injected into the chamber to displace the piston into the elastic tube. In the preferred embodiment, the elastic tube is made from a pliable rubber.

Because it is compressed by the concentric expansion of the tube while held inside the axial space, the stent is uniformly and evenly crimped onto the balloon catheter. Once the present invention tool has been operated up to a predetermined pressure, the pressure can be released to depressurize the chamber thereby removing the axial force on the elastic tube. Once the piston and chamber return to atmospheric pressure, the balloon catheter with the crimped stent can be withdrawn from the tool.

In an alternative embodiment, the present invention tool may use a mechanical drive source instead of the hydraulic drive source. In this embodiment, the piston is driven by a power screw that is threaded to the chassis. The power screw can be turned manually or by an electric motor. Rotation of the power screw drives the piston into the elastic tube to crimp the stent. Then counter-rotation of the power screw relieves the pressure on the piston to release the crimped stent.

An advantage of the present invention is that the elastomeric tube compresses somewhat for various types of catheters. The present invention is thus versatile and addresses the physician's desire to use many different catheter configurations for one style of stent.

In alternative embodiments of the present invention (not shown), the elastomeric tube can have various geometries. For example, the elastomeric tube can be fabricated to have a star-shaped cross-section, or it can be fashioned to have beveled ends. Rigid plastic fillet inserts can be placed adjacent the elastomeric tube within the chassis at the opposite ends to concentrate stress. The durometer hardness of the elastomeric tube can also be changed depending on the mechanical properties and design of the various stents to be crimped. The present invention further contemplates an elastomeric tube that can apply circumferential pressure on the stent, perhaps with use of bands or rings disposed along the circumference of the tube.

Therefore, the present invention crimping tool is highly versatile. It is useful to cardiologists and such physicians who are constantly concerned with proper deployment of the stent within the patient. With a consistently and reliably crimped stent as achieved by the present invention, proper deployment is possible. The present invention tool is further a time saver in that the stent crimping procedure can be performed fairly efficiently and quickly.

In addition, precise control of the pressure inside the chamber translates to precise control of the amount of compression exerted by the elastic tube on the stent. Consequently, the uniformity and degree of crimping of the stent can be controlled. These and other advantages of the present invention will become apparent from the following detailed description thereof when taken in conjunction with the accompanying drawings.

DETAILED DESCRIPTION OF THE PREFERRED EMBODIMENTS

Figure 1:
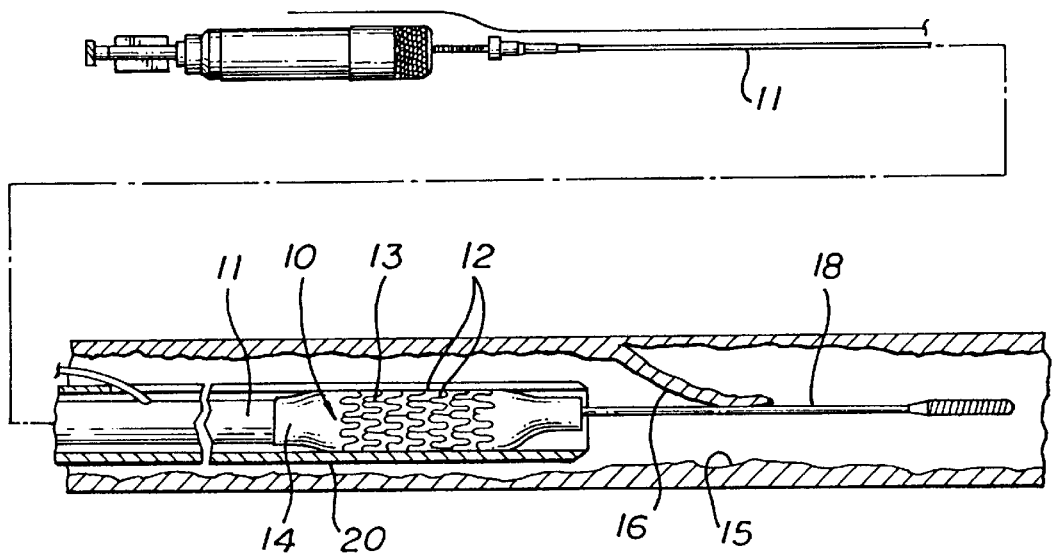
FIG. 1 is an elevational view, partially in section, depicting a stent that has been crimped onto a delivery catheter and disposed within a damaged vessel.

FIG. 1 illustrates intravascular stent 10 which is mounted onto delivery catheter 11. Stent 10 generally comprises a plurality of radially expandable cylindrical elements 12 disposed generally coaxially and interconnected by members 13 disposed between adjacent cylindrical elements 12. Delivery catheter 11 has an expandable portion or balloon 14 for expanding stent 10 within artery 15 or other vessel. Artery 15, as shown in FIG. 1, has dissected lining 16 which has occluded a portion of the arterial passageway.

Delivery catheter 11 onto which stent 10 is mounted is essentially the same as a conventional balloon dilatation catheter for angioplasty procedures. Balloon 14 may be formed of suitable materials such as polyethylene, polyethylene terephthalate, polyvinyl chloride, and other like polymers. In order for stent 10 to remain in place on balloon 14 during delivery to the site of the damage within artery 15, stent 10 is compressed onto balloon 14. This compressing step is known as crimping.

An optional retractable protective delivery sleeve 20 may be provided to further ensure that stent 10 stays in place on balloon 14 of delivery catheter 11 and to prevent abrasion of the body lumen by the open surface of stent 10 during delivery to the desired arterial location. Other means for securing stent 10 onto balloon 14 may also be used, such as providing collars or ridges on the ends of the working portion, i.e., the cylindrical portion of balloon 14. In order to implant stent 10, it is first mounted onto inflation balloon 14 on the distal extremity of delivery catheter 11. Stent 10 is crimped down onto balloon 14 to ensure a low profile. The present invention addresses this crimping procedure.

The catheter-stent assembly can be introduced into the patient's vasculature through processes known in the art. Briefly, guide wire 18 is disposed across the damaged arterial section with the detached or dissected lining 16 and the catheter-stent assembly is advanced over guide wire 18 within artery 15 until stent 10 is directly under detached lining 16. Prior to inflation of balloon 14, delivery sleeve 20 is retracted to expose stent 10. Balloon 14 of delivery catheter 11 is then inflated using an inflation fluid. Expansion of balloon 14 in turn expands stent 10 against artery 15. Next, balloon 14 is deflated and catheter 11 is withdrawn leaving stent 10 to support the damaged arterial section. As mentioned above, in order to ensure proper seating of stent 10 on balloon 14, and to ensure proper deployment of stent 10 at the site of the damage within artery 15, the stent crimping procedure is highly critical.

Figure 2:
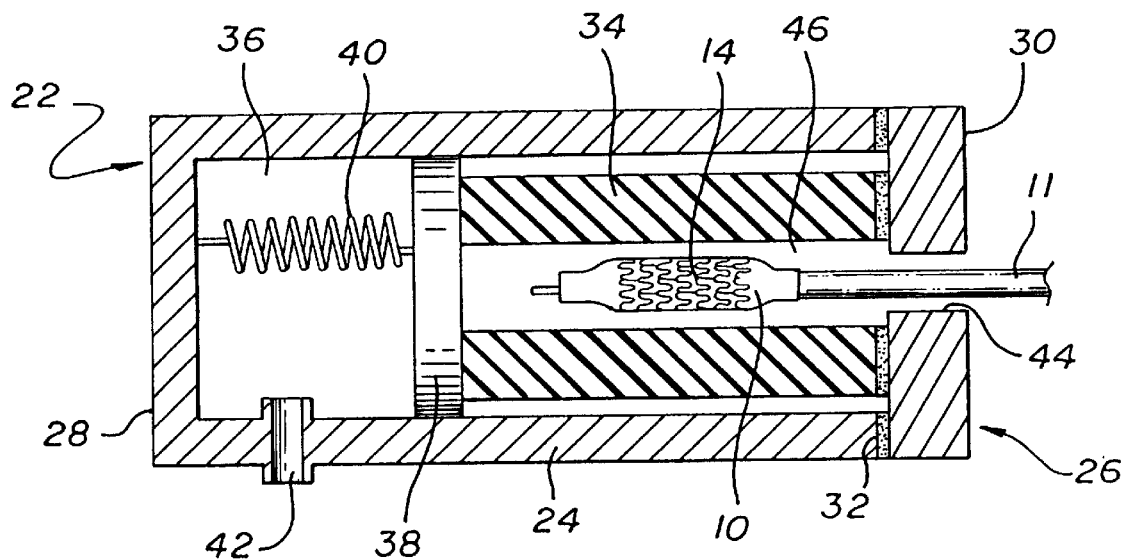
FIG. 2 is a side elevational sectional view of a preferred embodiment of the present invention stent crimping tool.

FIG. 2 provides a side elevational sectional view of a preferred embodiment of the present invention stent crimping tool 22. In the preferred embodiment shown, stent crimping tool 22 is constructed from cylindrical shape chassis 24 having open end 26 and closed end 28. Open end 26 is sealed closed with optional end cap 30 that is bonded to open end 26 using adhesive 32 of a type known in the art.

Within cylindrical shape chassis 24 is a hollow interior that contains a resilient or pliant elastic tube 34 that is preferably coaxially disposed within chassis 24. Notably, in the exemplary embodiment, elastic tube 34 has a length that is shorter than the interior of chassis 24. Because of this difference in length, and because elastic tube 34 is disposed adjacent open end 26, chamber 36 is formed adjacent closed end 28. Slidably disposed within chamber 36 is movable piston 38.

Figure 5:
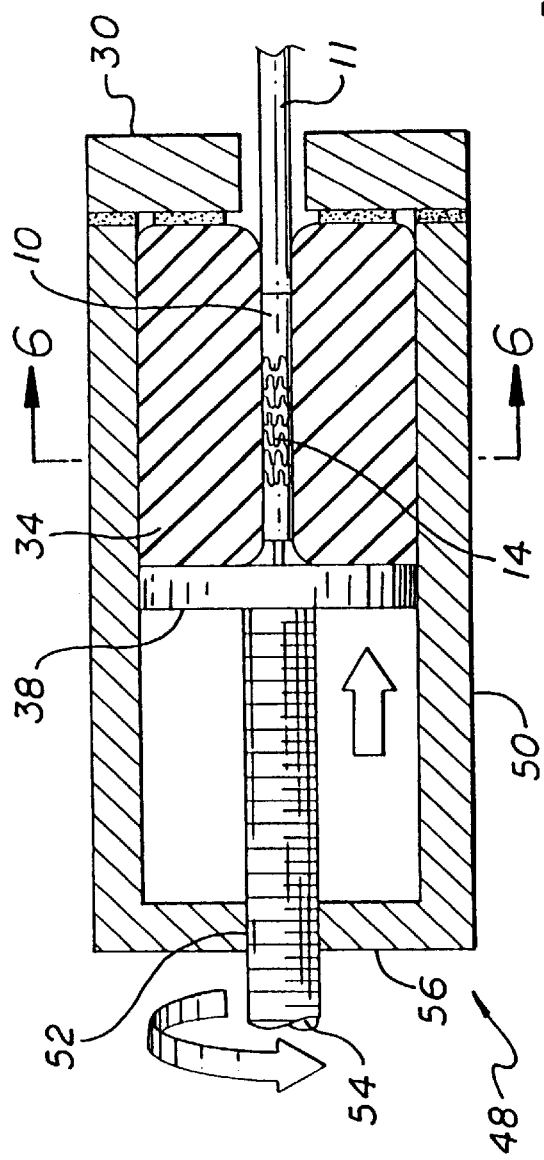
FIG. 5 is a side elevational sectional view of an alternative embodiment of the present invention, which uses a power screw to drive the piston into the tube.
Figure 6:
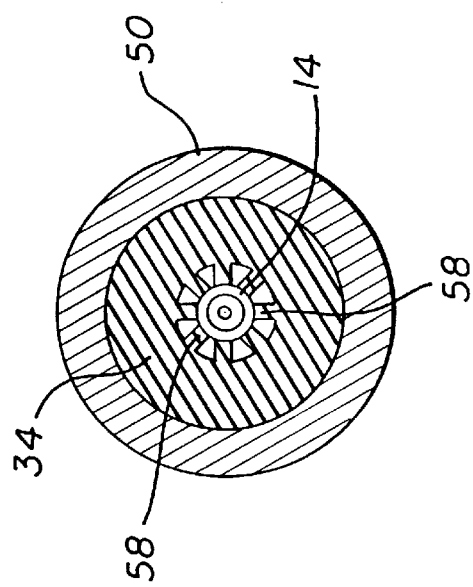
FIG. 6 is a cross-sectional end view taken along line 6—6 of FIG. 5 to show longitudinal striations within the elastic tube.

As best seen in the cross-sectional end view of FIG. 6, taken along line 6—6 of FIG. 5, elastic tube 34 includes optional striations 58 that preferably extend longitudinally along the length thereof. Conceptually, striations 58 are made from cuts or grooves formed along the inside diameter of elastic tube 34. Striations 58 act as stress concentrators that essentially define the geometry of axial space 46. As depicted in FIG. 6, striations 58 engage the stent-catheter assembly during the crimping process. Other shapes and lengths of striations 58 are contemplated, including a helical pattern, serpentine pattern, zig zag pattern, etc. The striations may further have bumps or contours to apply stress to specific zones along the stent-catheter assembly.

Optional compression spring 40 biases piston 38 into contact with elastic tube 34. Other mechanisms known in the art can be used to support piston 38 to prevent it from rattling or loosely moving within chamber 36. For example, in an alternative embodiment, rails and a dove tail can be formed into an outer circumference of the piston, respectively, allowing the piston to traverse longitudinally without losing its alignment and contact with the elastic tube. In yet another alternative embodiment, the dimensional tolerances between the chassis and piston are close, and the movable piston has a large thickness to maintain its alignment within the chassis. In this embodiment, the piston can traverse within the chamber without use of the optional compression spring or other support structure.

In the preferred embodiment, chamber 36 is hermetically sealed except for port 42 disposed between piston 38 and closed end 28. Port 42 is preferably connected to an indeflator (not shown), known in the art, which is used to inject a pressurized fluid into chamber 36.

End cap 30 includes central opening 44 that is aligned with axial space 46 of elastic tube 34. Central opening 44 allows the stent-catheter assembly to be inserted into the present invention tool 22 prior to undergoing the crimping procedure.

Leading up to the crimping procedure, a user introduces stent 10 already loaded onto balloon portion 14 of catheter 11 into axial space 46 within elastic tube 34. In the exemplary embodiment, the inside diameter of elastic tube 34 is slightly greater than the outside diameter of the uncrimped stent 14.

Figure 3:
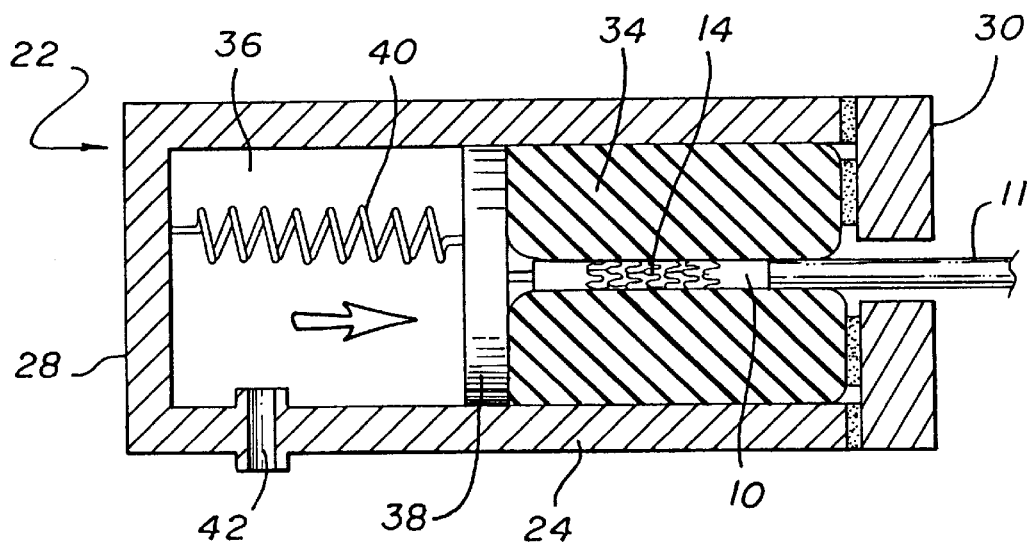
FIG. 3 is a side elevational sectional view of the present invention during operation of the tool when the stent is being crimped onto a balloon catheter.

FIG. 3 is a side elevational sectional view of stent crimping tool 22 shown in FIG. 2 undergoing the stent crimping process. In particular, port 42 is connected to the indeflator which has injected fluid into chamber 36. Pressures may range from one atmosphere in the unpressurized state of FIG. 2 to approximately three atmospheres in the pressurized state in FIG. 3. The increasing pressure inside chamber 36 displaces piston 38 into elastic tube 34.

As a result, elastic tube 34 is compressed axially or lengthwise. The elastic material of elastic tube 34 must maintain a constant volume due to its surface elasticity and containment within the confines of chassis 24. Continuous compression of elastic tube 34 by piston 38 causes the material of elastic tube 34 to displace axially and then radially into axial space 46 within elastic tube 34. This decreases the diameter of axial space 46.

In turn, stent 10 contained inside axial space 46 is compressed radially onto balloon portion 14 of catheter 11, as seen in FIG. 3. The arrows of FIG. 3 indicate movement of the material consisting of the elastic tube 34, wherein elastic tube 34 is contained in all directions except radially inward toward the center of axial space 46.

Once stent 10 is crimped onto balloon 14, the pressure supplied by the indeflator can be released by reversing the flow out port 42. Natural resilience of elastic tube 34 causes it to re-assume its initial shape thereby opening up axial space 46 an deflecting piston 38 in the opposite direction. Once axial space 46 re-assumes its original diameter, the crimped stent-catheter assembly can be withdrawn out of tool 22 through central opening 44.

Figure 4:
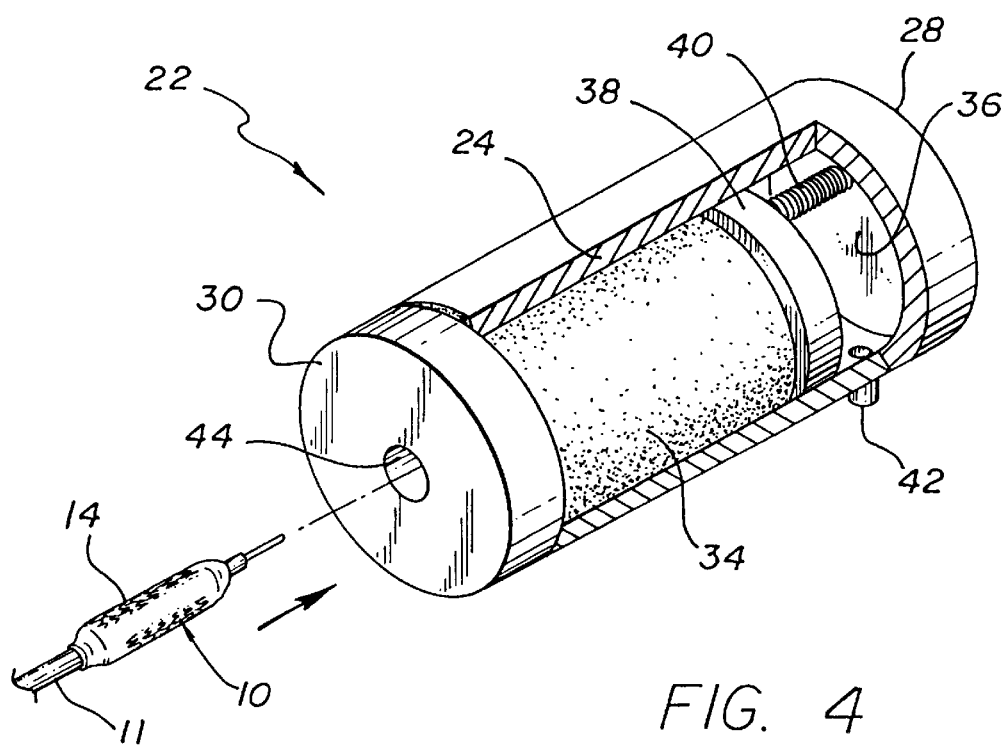
FIG. 4 is a partial cut-away, perspective view of a preferred embodiment of the present invention stent crimping tool.

FIG. 4 is a perspective view of a preferred embodiment of the present invention stent crimping tool 22. The partial cut-away view of FIG. 4 exposes the internal components of cylindrical shape chassis 24. As best seen in this figure, elastic tube 34 has a cylindrical shape contained by the inside diameter of cylindrical shape chassis 24. Abutting the back end of elastic tube 34 is piston 38. Directly behind piston 38 is hermetically sealed chamber 36 adjacent closed end 28. Flow into and out of chamber 36 is controlled by port 42 which may optionally be modified with a control valve known in the art. The stent-catheter assembly is inserted through central opening 44 into tool 22 to undergo the crimping process.

The present invention tool 22 is designed to be used inside a cath lab to crimp stents 10 onto balloon catheters 11 by exerting pressure evenly around stent 10 while it is correctly positioned on balloon 14 of catheter 11. Once the uncrimped stent-balloon catheter assembly is properly inserted inside axial space 46 of elastic tube 34, the assembly is locked into place by an optional snap lock, known in the art, at end cap 30. After catheter 11 is locked in place thus ensuring that stent 10 does not change position during the crimping process, the indeflator can be attached to port 42. The indeflator is used to increase the pressure inside chamber 36 which in turn exerts pressure on piston 38, which compresses elastic tube 34. As explained, the inside diameter of elastic tube 34 decreases, compressing stent 10 onto balloon 14 of catheter 11. The decreasing inside diameter of elastic tube 14 during compression is fairly homogeneous thus, evenly and uniformly compressing stent onto balloon 14.

Once tool 22 has undergone a predetermined pressure increase inside chamber 36, the pressure can be released. The pressurization of chamber 36 can be repeated or terminated. Once terminated, the pressure exerted by piston 38 on elastic tube 34 is eliminated allowing elastic tube 34 to return to its original unstressed shape. Axial space 46 reforms and the crimped stent-catheter assembly can be withdrawn.

The present invention as explained above can be actuated using a hydraulic drive source to move the piston. FIG. 5 provides a side elevational cross-sectional view of an alternative embodiment which uses a mechanical drive source to actuate the piston. In this exemplary embodiment of stent crimping tool 48 the construction is very similar to the hydraulically driven tool 22, although chassis 50 no longer requires port 42. Also, threaded opening 52 is formed in closed end 56. Power screw 54 is threaded through opening 52 and engages piston 38. Power screw 54 can be rotated manually by a crank, electrically by a motor, through an impeller driven by an indeflator, or by other means known in the art. Rotation of power screw 54 displaces piston 38 into elastic tube 34 in a manner akin to the influx of fluid in the previous embodiment. Elastic tube 34 is compressed axially and, through the same mechanism described above, stent 10 is crimped on to balloon 14. Counter-rotation of power screw 54 retracts piston 38 and relieves pressure on elastic tube 34. The crimping cycle can be repeated, or the crimped stent-catheter assembly can be removed from tool 48.

The present invention crimping tool is preferably made from injection molded plastics and rubber. In an alternative embodiment, it is possible to use translucent or transparent polymers so that the crimping process can be monitored visually. The present invention design is also well suited to be made from surgical steel or like metals.

In alternative embodiments of the present invention (not shown), the elastic tube can assume various geometries. For example, the elastic tube can be fabricated to have a star-shaped cross-section, or it can be fashioned to have beveled ends. At those beveled ends of the elastic tube, the void created between the beveled surface and the inside walls of the tubular chassis, piston, and end cap, can be filled with a rigid, plastic, fillet insert to help concentrate compression of the elastic tube.

Figure 7B:
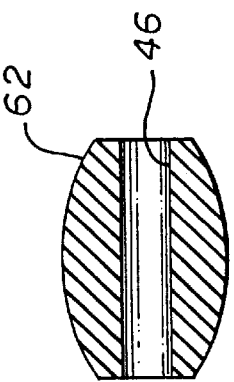
FIGS. 7A and 7B are side elevational views in cross-section of alternative embodiments of the elastic tube having varying diameters.
Figure 7A:
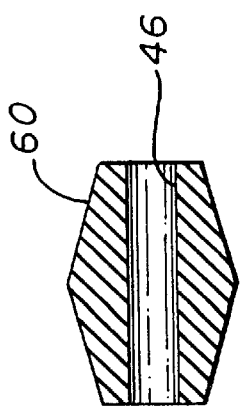

Still other alternative embodiments of the elastic tube may have an outside diameter that varies along the length thereof. This is shown in FIGS. 7A and 7B, which are side elevational views taken in cross-section. In FIG. 7A, elastic tube 60 has a dual cone profile, while in FIG. 7B, elastic tube 62 has an ovoid profile. A single cone profile is also contemplated, although not shown. During the crimping process, the particular outside geometry helps concentrate stress at specific regions of the stent-catheter assembly when it is positioned within axial space 46.

The elastic tube is preferably made from an elastomer. As such, the durometer hardness/toughness of the elastic/elastomeric tube can be changed depending on the mechanical properties and design of the various stents to be crimped. The present invention also contemplates an elastic tube that can apply circumferential pressure on the stent, perhaps with use of bands or rings disposed along the circumference of the elastic tube.

As is appreciated by those skilled in the art, the present invention stent crimping tool is designed both for single use applications in a cath lab by a physician, or for multiple use applications in a sterile environment in a high volume manufacturing facility. In the latter scenario, where sterile conditions exist, the stent crimping tool can be used repeatedly to crimp stents onto balloons until the elasticity in the elastic tube is worn or the hermetic seal in the chamber is broken. Repeated uses are therefore contemplated for the present invention in controlled sterile environments. On the other hand, single use applications are contemplated in the present invention and are required when used by cath lab personnel.

Other modifications can be made to the present invention without departing from the scope thereof. The specific dimensions, procedural steps, and materials of construction are provided as examples, and substitutes are readily contemplated which do not depart from the invention.

What is claimed is:

1. A tool for crimping a stent in combination with a stent, the combination comprising;

the tool having a rigid chassis, the rigid chassis having a hollow interior, a front end, and a back end;

a back end cap enclosing the back end of the chassis;

a front end cap having a first central opening and enclosing the front end of the chassis;

an elastic tube having a second central opening extending therethrough and having a length less than the length of the hollow interior to define a chamber adjacent to the back end, the elastic tube being disposed within the hollow interior and adjacent the front end cap such that the second central opening is in axial alignment with the first central opening;

a piston slidably disposed within the chamber; and a drive source engaging the rigid chassis and the piston and disposed within the hollow interior, so as to displace the piston to compress the elastic tube;

wherein the stent is mounted on a balloon catheter and is positioned within the second central opening of the elastic tube, and upon actuation of the drive source, the piston compresses the elastic tube thereby squeezing the stent radially onto the catheter.

2. The combination of claim 1, wherein the tool further comprises a port in communication with the chamber disposed between the back end of the chassis and the piston, and the drive source includes a pressurized fluid, wherein a flow from the pressurized fluid source connected to the port forces the piston into and compresses the elastic tube.

3. The combination of claim 1, wherein the elastic tube includes a varying outside diameter.

4. The combination of claim 2, wherein the pressurized fluid source includes an indeflator.

5. The combination of claim 1, wherein the front end cap is bonded to the chassis.

6. The combination of claim 1, wherein the elastic tube includes a polymer.

7. The combination of claim 1, wherein the elastic tube has a profile that includes a cone.

8. The combination of claim 1, wherein the elastic tube includes at least one striation formed in an inside diameter.

9. The combination of claim 2, wherein the pressurized fluid source includes an inflation fluid.

10. The combination of claim 1, wherein an inside diameter of the hollow interior of the elastic tube is slightly greater than an outside diameter of the uncrimped stent.

11. The combination of claim 1, wherein the drive source includes a power screw threaded to the closed back end.

12. A tool for crimping a stent in combination with a stent, the combination comprising;
    a rigid chassis having an interior of a length closed at an end and open at the opposite end;
    an end cap covering the open end, the end cap having a central opening;
    a pliant tube disposed within the rigid chassis adjacent to the end cap having an axial space in communication with the central opening of the end cap, wherein the tube has an axial length that is less than the length of the interior of the chassis forming a chamber adjacent the closed end;
    a piston slidably disposed within the chamber of the rigid chassis; and
    a drive source engaging the rigid chassis at the closed end and the piston and disposed within the chamber, wherein the stent is mounted on a catheter and positioned through the central opening within the axial space, and the drive source displaces the piston to compress the pliant tube and the compressed pliant tube squeezes the stent radially onto the catheter.

13. The combination of claim 12, wherein the drive source includes a pressurized fluid source, and the rigid chassis includes a port in fluid communication with chamber connected to the pressurized fluid source, whereby the pressurized fluid source displaces the piston.

14. The combination of claim 12, wherein the drive source includes a power screw threaded to the closed end of the rigid chassis.

15. The combination of claim 13, wherein the pressurized fluid source includes an indeflator.

16. The combination of claim 12, wherein the piston and the end cap abut the pliant tube.

17. The combination of claim 12, wherein the chamber is hermetically sealed.

18. The combination of claim 12, wherein chassis and pliant tube have circular cross-sections and are coaxially disposed.

19. A method for crimping a stent onto a balloon catheter comprising the steps of:
    providing a chassis having an interior enclosed at an end and open at an opposite end;
    enclosing the open end with an end cap having a central opening;
    providing a resilient tube inside the interior having a length shorter than a length of the interior thereby forming a chamber adjacent the enclosed end of the housing, wherein the resilient tube includes an axial space in communication with the central opening;
    providing a piston within the cylinder;
    loading the stent onto the balloon catheter;
    inserting the stent and catheter into the axial space; and
    displacing the piston against the resilient tube to compress the tube;
    wherein the compressed resilient tube compresses the stent radially onto the catheter.

20. The method of claim 19, wherein the step of displacing the piston further comprises injecting a fluid under pressure through a port in the chassis in communication with the chamber between the enclosed end and the piston, whereby the pressurized fluid source displaces the piston into the resilient tube thereby compressing the resilient tube.

21. The method of claim 19, wherein the step of displacing the piston further comprises providing a power screw engaging the enclosed end and the piston, and rotating the power screw to displace the piston.

22. The method of claim 20, wherein the step of injecting a fluid under pressure includes the step of connecting an indeflator to the chamber.

23. The method of claim 19, wherein the resilient tube includes rubber.

24. The method of claim 19, wherein the method further comprises the step of bonding the end cap to the chassis and the resilient tube.

25. The method of claim 19, wherein the axial space has a diameter slightly greater than an outside diameter of the unexpanded stent.

26. The method of claim 20, wherein the method further comprises the steps of depressurizing the chamber allowing the elastic tube to restore to its original shape and re-pressurizing the chamber.

27. The method of claim 19, wherein the elastic tube includes an internal striation.

28. The method of claim 19, wherein the elastic tube has a varying outside diameter.

* * * * *

UNITED STATES PATENT AND TRADEMARK OFFICE
CERTIFICATE OF CORRECTION

PATENT NO. : 6,009,614
DATED : Jan. 4, 2000
INVENTOR(S) : Stephen A. Morales

It is certified that error appears in the above-identified patent and that said Letters Patent is hereby corrected as shown below:

Title page, under "ABSTRACTS", line 8 of text, change "ofthe", to read --of the--.

Title page, page 2, after "5,653,691   8/1997   Rupp et al.", add --5,672,169   9/1997   Verbeek--.

Signed and Sealed this

Fifteenth Day of August, 2000

Attest:

Q. TODD DICKINSON

Attesting Officer    *Director of Patents and Trademarks*